(12) United States Patent
Goldman

(10) Patent No.: US 8,329,145 B1
(45) Date of Patent: Dec. 11, 2012

(54) USE OF COOLING AGENT TO IMPROVE COSMETICS

(75) Inventor: Allen S. Goldman, Canton, MA (US)

(73) Assignee: Skindinavia, Inc., Canton, MA (US)

( * ) Notice: Subject to any disclaimer, the term of this patent is extended or adjusted under 35 U.S.C. 154(b) by 157 days.

(21) Appl. No.: 13/009,536

(22) Filed: Jan. 19, 2011

Related U.S. Application Data

(60) Provisional application No. 61/345,727, filed on May 18, 2010, provisional application No. 61/422,433, filed on Dec. 13, 2010.

(51) Int. Cl.
*A61Q 1/00* (2006.01)

(52) U.S. Cl. .......................................... 424/43; 424/401

(58) Field of Classification Search ........................ None
See application file for complete search history.

(56) References Cited

OTHER PUBLICATIONS

Label from a product on sale in Jan. 2007.

*Primary Examiner* — Jyothsna Venkat
(74) *Attorney, Agent, or Firm* — Pandiscio & Pandiscio

(57) ABSTRACT

A pumpable liquid spray formulation for retarding degradation of color cosmetics.

6 Claims, No Drawings

USE OF COOLING AGENT TO IMPROVE COSMETICS

REFERENCE TO PENDING PRIOR PATENT APPLICATIONS

This patent application claims benefit of:

(i) pending prior U.S. Provisional Patent. Application Ser. No. 61/345,727, filed May 18, 2010 by Allen Goldman for USE OF COOLING FLUID TO EXTEND MAKEUP WEAR, LUMINOSITY, AND MOISTURIZATION, AND TO REDUCE SURFACE SHINE; and (ii) pending prior U.S. Provisional Patent Application Ser. No. 61/422,433, filed Dec. 13, 2010 by Allen S. Goldman for USE OF COOLING AGENT TO IMPROVE COSMETICS AND OTHER SKIN-APPLIED PRODUCTS.

The two (2) above-identified patent applications are hereby incorporated herein by reference.

FIELD OF THE INVENTION

This invention relates to cosmetics in general, and more particularly to the use of a cooling agent to improve cosmetics.

BACKGROUND OF THE INVENTION

Color cosmetics are used to enhance facial appearance and cover facial imperfections. Examples of such color cosmetics include, but are not limited to, foundation, eye shadow, blush, and concealer.

Color cosmetics typically degrade over time. The rate of degradation can be influenced by a number of factors including, but not limited to, ingredient characteristics, user skin type, skin temperature, the temperature of the surrounding environment, humidity of the surrounding environment, etc. Since such degradation undermines the appearance of the color cosmetics, it is generally desirable that the color cosmetics resist such degradation.

To this end, a number of color cosmetic manufacturers have created "extended wear" products (e.g., foundations, mascaras, eye shadows, etc.). However, many users find these extended wear products to be only partially satisfactory, since (i) they are typically available in only a limited range of colors and shades, (ii) they are generally difficult to remove, and (iii) they typically have an unnatural "feel" (i.e., the extended wear products generally do not offer the same "lightweight" feel that standard color cosmetics offer).

Alternatively, users may also use a "make-up setting spray" to extend the wear of their color cosmetics. Such make-up setting sprays are applied as a surface layer over the color cosmetics and act as a protective coating to help prevent degradation of the color cosmetics. However, such make-up setting sprays tend to stiffen the make-up, which can result in user discomfort. Furthermore, such make-up setting sprays typically comprise polymers (e.g., acrylics) dissolved in a solvent (e.g., alcohol), which produces a clear, lacquer-like coating on the make-up, which can appear unnatural and feel uncomfortable. And some people find that the solvent (e.g., alcohol) used in these make-up setting sprays can be an irritant to their skin.

Thus there is a need for a new way to extend the wear of make-up which does not suffer from the aforementioned limitations of the prior art.

SUMMARY OF THE INVENTION

The present invention provides a new way to extend the wear of make-up which does not suffer from the aforementioned limitations of the prior art.

More particularly, the present invention comprises the provision and use of a novel pumpable liquid spray formulation which is sprayed over the color cosmetics, after the color cosmetics have been applied to the skin, so as to retard degradation of the color cosmetics and thereby extend make-up wear. This novel formulation may comprise a suspension containing, among other things, a novel cooling agent. The novel cooling agent comprises a volatile component which slowly evaporates during use, thereby providing "evaporative cooling" to the color cosmetics. This evaporative cooling significantly reduces the rate at which moisture and/or other volatiles migrate out of the color cosmetics, thereby significantly extending the useful life of the color cosmetics.

In one preferred form of the present invention, the novel cooling agent comprises a volatile hydroether (e.g., methyl perfluorobutyl ether and methyl perfluoroisobutyl ether), either alone or in combination with a carrier (e.g., polyhydroxystearic acid) which serves to deliver the volatile hydroether to the color cosmetics. The volatile hydroether (i.e., the novel cooling agent) can be contained in, and delivered by, microcapsules which, when ruptured, release the volatile hydroether. In essence, as water in the spray starts to evaporate, the carrier (e.g., the polyhydrostearic acid) starts to give up the volatile hydroether (e.g., methyl perfluorobutyl ether and methyl perfluoroisobutyl ether).

If desired, the methyl perfluorobutyl ether and/or methyl perfluoroisobutyl ether can be replaced by perfluoroisohexane, perfluoro poly ether and/or hydro fluoro poly ether.

In one preferred manner of use, the color cosmetics are applied to the skin of the user; and then the pumpable liquid spray formulation is applied to the color cosmetics as an aerosol mist while the color cosmetics are on the skin of the user.

Alternatively, and/or additionally, the novel formulation can be applied to the skin prior to the application of the color cosmetics so as to extend the useful life of the color cosmetics.

In one preferred form of the invention, there is provided a pumpable liquid spray formulation for retarding degradation of color cosmetics, the pumpable liquid spray formulation comprising:

water, 82.228% by weight;
alcohol denat, 9.0% by weight;
polyhydroxystearic acid, 2.23% by weight;
pvp, 2.0% by weight;
methyl perfluorobutyl ether, 1.25% by weight;
methyl perfluoroisobutyl ether, 1.25% by weight;
dimethicone peg-7 phosphate, 0.75% by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±2% of their stated value.

In another preferred form of the invention, there is provided a method for improving cosmetic wear, the method comprising:

providing a pumpable liquid spray formulation for retarding degradation of color cosmetics, the pumpable liquid spray formulation comprising:
  water, 82.228% by weight;
  alcohol denat, 9.0% by weight;
  polyhydroxystearic acid, 2.23% by weight;
  pvp, 2.0% by weight;
  methyl perfluorobutyl ether, 1.25% by weight;
  methyl perfluoroisobutyl ether, 1.25% by weight;
  dimethicone peg-7 phosphate, 0.75% by weight;
  ppg-3 benzyl ether myristate, 0.5% by weight;
  caprylyl glycol, 0.5% by weight;
  methyl methacrylate cross polymer, 0.12% by weight;
  sodium hydroxide, 0.07% by weight;
  sodium cocamidopropyl pg dimonium chloride phosphate, 0.05% by weight;
  glycereth-5 lactate, 0.01% by weight;
  N,2,3-trimethyl-2-isopropyl butamide, 0.01% by weight;
  ethylhexyl isononanoate, 0.01% by weight;
  isononyl isononanoate, 0.01% by weight;
  fragrance, 0.01% by weight;
  aloe barbandensis leaf extract, 0.001% by weight; and
  poloxamer 407, 0.001% by weight;
  wherein all of the foregoing percentage weights have a tolerance band of ±2% of their stated value;
  applying color cosmetics to the skin of the user; and
  applying the pumpable liquid spray formulation to the color cosmetics, as an aerosol mist while the color cosmetics are on the skin of the user.

In another preferred form of the invention, there is provided a method for improving cosmetic wear, the method comprising:
providing a pumpable liquid spray formulation for retarding degradation of color cosmetics, the pumpable liquid spray formulation comprising:
  water, 82.228% by weight;
  alcohol denat, 9.0% by weight;
  polyhydroxystearic acid, 2.23% by weight;
  pvp, 2.0% by weight;
  methyl perfluorobutyl ether, 1.25% by weight;
  methyl perfluoroisobutyl ether, 1.25% by weight;
  dimethicone peg-7 phosphate, 0.75% by weight;
  ppg-3 benzyl ether myristate, 0.5% weight;
  caprylyl glycol, 0.5% by weight;
  methyl methacrylate cross polymer, 0.12% by weight;
  sodium hydroxide, 0.07% by weight;
  sodium cocamidopropyl pg dimonium chloride phosphate, 0.05% by weight;
  glycereth-5 lactate, 0.01% by weight;
  N,2,3-trimethyl-2-isopropyl butamide, 0.01% by weight;
  ethylhexyl isononanoate, 0.01% by weight;
  isononyl isononanoate, 0.01% by weight;
  fragrance, 0.01% by weight;
  aloe barbandensis leaf extract, 0.001% by weight; and
  poloxamer 407, 0.001% by weight;
  wherein all of the foregoing percentage weights have a tolerance band of ±2% of their stated value;
  applying the pumpable liquid spray formulation to the skin of the user as an aerosol mist; and
  applying color cosmetics to the skin of the user over the pumpable liquid spray formulation.

In another preferred form of the invention, there is provided a pumpable liquid spray formulation for retarding degradation of color cosmetics, the pumpable liquid spray formulation comprising:
  water, 82.728% by weight;
  alcohol denat, 9.0% by weight;
  polyhydroxystearic acid, 2.23% by weight;
  pvp, 2.0% by weight;
  perfluoroisohexane, 2.5% by weight;
  dimethicone peg-7 phosphate, 0.75% by weight;
  ppg-3 benzyl ether myristate, 0.5% by weight;
  caprylyl glycol, 0.5% by weight;
  methyl methacrylate cross polymer, 0.12% by weight;
  sodium hydroxide, 0.07% by weight;
  sodium cocamidopropyl pg dimonium chloride phosphate, 0.05% by weight;
  glycereth-5 lactate, 0.01% by weight;
  N,2,3-trimethyl-2-isopropyl butamide, 0.01% by weight;
  ethylhexyl isononanoate, 0.01% by weight;
  isononyl isononanoate, 0.01% by weight;
  fragrance, 0.01% by weight;
  aloe barbandensis leaf extract, 0.001% by weight; and
  poloxamer 407, 0.001% by weight;
  wherein all of the foregoing percentage weights have a tolerance band of ±2% of their stated value.

In another preferred form of the invention, there is provided a method for improving cosmetic wear, the method comprising:
providing a pumpable liquid spray formulation for retarding degradation of color cosmetics, the pumpable liquid spray formulation comprising:
  water, 82.228% by weight;
  alcohol denat, 9.0% by weight;
  polyhydroxystearic acid, 2.23% by weight;
  pvp, 2.0% by weight;
  perfluoroisohexane, 2.5% by weight;
  dimethicone peg-7 phosphate, 0.75% weight;
  ppg-3 benzyl ether myristate, 0.5% by weight;
  caprylyl glycol, 0.5% by weight;
  methyl methacrylate cross polymer, 0.12% by weight;
  sodium hydroxide, 0.07% by weight;
  sodium cocamidopropyl pg dimonium chloride phosphate, 0.05% by weight;
  glycereth-5 lactate, 0.01% by weight;
  N,2,3-trimethyl-2-isopropyl butamide, 0.01% by weight;
  ethylhexyl isononanoate, 0.01% by weight;
  isononyl isononanoate, 0.01% by weight;
  fragrance, 0.01% by weight;
  aloe barbandensis leaf extract, 0.001% by weight; and
  poloxamer 407, 0.001% by weight;
  wherein all of the foregoing percentage weights have a tolerance band of ±2% of their stated value;
  applying color cosmetics to the skin of the user; and
  applying the pumpable liquid spray formulation to the color cosmetics, as an aerosol mist while the color cosmetics are on the skin of the user.

In another preferred form of the invention, there is provided a method for improving cosmetic wear, the method comprising:
providing a pumpable liquid spray formulation for retarding degradation of color cosmetics, the pumpable liquid spray formulation comprising:
  water, 82.228% by weight;
  alcohol denat, 9.0% by weight;
  polyhydroxystearic acid, 2.23% by weight;
  pvp, 2.0% by weight;
  perfluoroisohexane, 2.5% by weight;
  dimethicone peg-7 phosphate, 0.75% weight;
  ppg-3 benzyl ether myristate, 0.5% weight;
  caprylyl glycol, 0.5% by weight;
  methyl methacrylate cross polymer, 0.12% by weight;
  sodium hydroxide, 0.07% by weight;

sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±2% of their stated value;
applying the pumpable liquid spray formulation to the skin of the user as an aerosol mist; and
applying color cosmetics to the skin of the user over the pumpable liquid spray formulation.

DETAILED DESCRIPTION OF THE INVENTION

The present invention provides a new way to extend the wear of make-up which does not suffer from the aforementioned limitations of the prior art.

More particularly, the present invention comprises the provision and use of a novel pumpable liquid spray formulation which is sprayed over the color cosmetics, after the color cosmetics have been applied to the skin, so as to retard degradation of the color cosmetics and thereby extend make-up wear. This novel formulation may comprise a suspension containing, among other things, a novel cooling agent. The novel cooling agent comprises a volatile component which slowly evaporates during use, thereby providing "evaporative cooling" to the color cosmetics. This evaporative cooling significantly reduces the rate at which moisture and/or other volatiles migrate out of the color cosmetics, thereby significantly extending the useful life of the color cosmetics.

In one preferred form of the invention, the novel cooling agent comprises a volatile hydroether (e.g., methyl perfluorobutyl ether and methyl perfluoroisobutyl ether), either alone or in combination with a carrier (e.g., polyhydrostearic acid) which serves to deliver the volatile hydroether to the color cosmetics. The volatile hydroether (i.e., the novel cooling agent) can be contained in, and delivered by, microcapsules which, when ruptured, release the volatile hydroether. In essence, as water in the spray starts to evaporate, the carrier (e.g., the polyhydrostearic acid) starts to give up the volatile hydroether (e.g., methyl perfluorobutyl ether and methyl perfluoroisobutyl ether).

If desired, the methyl perfluorobutyl ether and/or methyl perfluoroisobutyl ether can be replaced by perfluoroisohexane, perfluoro poly ether and/or hydro fluoro poly ether. The perfluoro isohexane is 2.5% by weight.

In one preferred manner of use, the color cosmetics are applied to the skin of the user; and then the pumpable liquid spray formulation is applied to the color cosmetics as an aerosol mist while the color cosmetics are on the skin of the user.

Table I provides one preferred formulation for the novel pumpable liquid spray formulation of the present invention, wherein all of the percentage weights provided in Table I have a tolerance band of ±2% of their stated value. This pumpable liquid spray formulation comprises a suspension and has been found to provide an excellent "general purpose" cosmetic enhancer, particularly well-suited for "normal" skin types.

The specific purpose and benefits associated with each of the ingredients incorporated in the novel pumpable liquid spray formulation of the present invention are provided in Table I.

The following additional comments are made with respect to the ingredients incorporated in the novel pumpable liquid spray formulation of the present invention:
with respect to "water", water is a carrier of the technology, the more water used the finer and lighter the mist—it has been discovered that, for successful spray application, it is important that water constitute at least 82% (by weight) of the pumpable liquid spray formulation of the present invention;
with respect to "alcohol denat" (i.e., de-natured alcohol), this is preferably SPA Alcohol 40B 190 Proof;
the polyhydroxystearic acid is an encapsulating agent, the microcapsules release the cooling agent, if the cooling agent were not encapsulated in the polyhydroxystearic acid, the cooling agent would prematurely evaporate—in other words, the polyhydroxystearic acid comprises a foam burst stabilizer to add longer cooling for longer make-up wear, the polyhydroxystearic acid releases its encapsulated material when removed from an aqueous environment, i.e., when water in the spray evaporates—it has been discovered that, for proper cooling release, it is important that the polyhydrostearic acid comprise more than 2.0% (by weight) of the pumpable liquid spray formulation of the present invention;
the PVP (polyvinylpyrrolidone) is kept under a concentration of 3.0% (by weight) in order to provide a more natural look and a less shiny appearance—a lower concentration provides increased sprayability and reduces shine, since this component is a plasticizer and gives a sheen—in the preferred embodiment, the PVP is kept at a concentration of 2.0% by weight;
the methyl perfluorobutyl ether is an active ingredient for longer wear—for proper cooling, this component should comprise more than 1% (by weight) of the pumpable liquid spray formulation of the present invention;
the methyl perfluoroisobutyl ether is an active ingredient for longer wear—for proper cooling, this component should comprise more than 1% (by weight) of the pumpable liquid spray formulation of the present invention;
PPG-3 benzyl ether myristate is a varied pigment wetter to keep the make-up from clumping or sliding based on skin type;
caprylyl glycol is a preservative, it is important that this material not be replaced with phenoxyethanol, gluconolactone and/or sodium benzoate since such alternative ingredients have been found to cause irritation to users with sensitive skin;
the methyl methacrylate cross-polymer is an oil absorber and light diffuser, it is extremely important that it be finely ground (e.g., to an average particle size of 4.5-8.5 microns or less) in order to avoid clogging the sprayer which is used to apply the novel formulation to the color cosmetics—the methyl methacrylate cross-polymer is an anti-shine ingredient which may be increased for oily skin types and/or may be decreased for dry skin types, but in any case preferably constitutes less than 0.5% (by weight) of the pumpable liquid spray formulation of the present invention, and most preferably about 0.12% (by weight) of the pumpable liquid spray formulation;
the glycereth-5 lactate is a moisturizer, higher levels may be used for dry or mature skin;
the ethylhexyl isononanoate provides a cooling feature;
the isononyl isononoate provides a cooling feature;
the specific fragrance used can be varied according to customer preference, in one preferred form of the invention, the fragrance is Green Tea for a lighter scent and reduced skin irritation;

aloe barbandensis leaf extract is a moisturizer, higher levels may be used for dry or mature skin; and poloxamer 407 is a thickener and emollient, in practice it has been found that it is extremely important to include this ingredient in the formulation in order keep particulates and solids evenly dispersed within the suspension and prevent any settling out of the finely ground constituent components.

The present invention provides extended cooling of the color cosmetics, which extends their useful life and improves the overall appearance of the color cosmetics. Among other things, the present invention provides longer wear, increased user comfort, reduced moisture loss, increased make-up surface luminosity, reduced surface shine, etc. In fact, the present invention provides a cosmetic formulation such that the make-up generally looks as good at the end of the day as it did at the beginning of the day.

In the foregoing description, the new formulation is described as being applied to the color cosmetics after the color cosmetics have been applied to the skin. Alternatively, and/or additionally, the novel formulation can also be applied to the skin prior to the application of the color cosmetics so as to extend the useful life of the color cosmetics.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

TABLE I

| Ingredient | Purpose | % by weight |
| --- | --- | --- |
| WATER | solvent | 82.228 |
| ALCOHOL DENAT | solvent/antiseptic | 9 |
| POLYHYDROXYSTEARIC ACID | foam burst stabilizer | 2.23 |
| PVP | film former | 2 |
| METHYL PERFLUOROBUTYL ETHER | foam burst | 1.25 |
| METHYL PERFLUOROISOBUTYL ETHER | foam burst | 1.25 |
| DIMETHICONE PEG-7 PHOSPHATE | emulsifier for silicones, conditioned feeling on skin | 0.75 |
| PPG-3 BENZYL ETHER MYRISTATE | emollient, lubricant, high gloss, pigment wetting | 0.5 |
| CAPRYLYL GLYCOL | preservative | 0.5 |
| METHYL METHACRYLATE CROSS POLYMER | light diffusion, anti-shine, line reducer, oil absorber | 0.12 |
| SODIUM HYDROXIDE | PH Modifier | 0.07 |
| SODIUM COCAMIDOPROPYL PG DIMONIUM CHLORIDE PHOSPHATE | foam burst stabilizer | 0.05 |
| GLYCERETH-5 LACTATE | emollient, moisturizer | 0.01 |
| N,2,3-TRIMETHYL-2-ISOPROPYL BUTAMIDE | cooling agent | 0.01 |
| ETHYLHEXYL ISONONANOATE | dry feel emollient | 0.01 |
| ISONONYL ISONONANOATE | dry feel emollient | 0.01 |
| FRAGRANCE | | 0.01 |
| ALOE BARBANDENSIS LEAF EXTRACT | skin protectant, humectant, smoothing | 0.001 |
| POLOXAMER 407 | thickener | 0.001 |
| Totals | | 100 |

Note:
all of the foregoing percentage weights have a tolerance band of ±2% of their stated value

What is claimed is:

1. A pumpable liquid spray formulation for retarding degradation of color cosmetics, the pumpable liquid spray formulation consisting of:
water, 82.228 by weight;
alcohol denat, 9.0% by weight;
polyhydroxystearic acid, 2.23% by weight;
polyvinyl pyrrolidone (pvp), 2.0% by weight;
methyl perfluorobutyl ether, 1.25% by weight;
methyl perfluoroisobutyl ether, 1.25% by weight;
dimethicone peg-7 phosphate, 0.75 by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±2% of their stated value.

2. A method for improving cosmetic wear, the method comprising:
providing a pumpable liquid spray formulation for retarding degradation of color cosmetics, the pumpable liquid spray formulation consisting of:
water, 82.228% by weight;
alcohol denat, 9.0% by weight;
polyhydroxystearic acid, 2.23% by weight;
polyvinyl pyrrolidone (pvp), 2.0% by weight;
methyl perfluorobutyl ether, 1.25% weight;
methyl perfluoroisobutyl ether, 1.25% by weight;
dimethicone peg-7 phosphate, 0.75% by weight;
ppg-3 benzyl ether myristate, 0.5% weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±2% of their stated value;

applying color cosmetics to the skin of the user; and applying the pumpable liquid spray formulation to the color cosmetics, as an aerosol mist while the color cosmetics are on the skin of the user.

3. A method for improving cosmetic wear, the method comprising:
providing a pumpable liquid spray formulation for retarding degradation of color cosmetics, the pumpable liquid spray formulation consisting of:
water, 82.228% by weight;
alcohol denat, 9.0% by weight;
polyhydroxystearic acid, 2.73% by weight;
polyvinyl pyrrolidone (pvp), 2.0% by weight;
methyl perfluorobutyl ether, 1.25% weight;
methyl perfluoroisobutyl ether, 1.25% by weight;
dimethicone peg-7 phosphate, 0.75% by weight;
ppg-3 benzyl ether myristate, 0.5% weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±2% of their stated value;
applying the pumpable liquid spray formulation to the skin of the user as an aerosol mist; and
applying color cosmetics to the skin of the user over the pumpable liquid spray formulation.

4. A pumpable liquid spray formulation for retarding degradation of color cosmetics, the pumpable liquid spray formulation consisting of:
water, 82.228% by weight;
alcohol denat, 9.0% by weight;
polyhydroxystearic acid, 2.23% by weight;
polyvinyl pyrrolidone (pvp), 2.0% by weight;
perfluoroisohexane, 2.5% by weight;
dimethicone peg-7 phosphate, 0.75% by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±2% of their stated value.

5. A method for improving cosmetic wear, the method comprising:
providing a pumpable liquid spray formulation for retarding degradation of color cosmetics, the pumpable liquid spray formulation consisting of:
water, 82.228% by weight;
alcohol denat, 9.0% by weight;
polyhydroxystearic acid, 2.23% by weight;
polyvinyl pyrrolidone (pvp), 2.0% by weight;
perfluoroisohexane, 2.5% by weight;
dimethicone peg-7 phosphate, 0.75% by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±2% of their stated value;
applying color cosmetics to the skin of the user; and
applying the pumpable liquid spray formulation to the color cosmetics, as an aerosol mist while the color cosmetics are on the skin of the user.

6. A method for improving cosmetic wear, the method comprising:
providing a pumpable liquid spray formulation for retarding degradation of color cosmetics, the pumpable liquid spray formulation consisting of:
water, 82.228% by weight;
alcohol denat, 9.0% by weight;
polyhydroxystearic acid, 2.23% by weight;
polyvinyl pyrrolidone (pvp), 2.0% by weight;
perfluoroisohexane, 2.5% by weight;
dimethicone peg-7 phosphate, 0.75% by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±2% of their stated value;
applying the pumpable liquid spray formulation to the skin of the user as an aerosol mist; and
applying color cosmetics to the skin of the user over the pumpable liquid spray formulation.

* * * * *